(12) United States Patent
Uhrig

(10) Patent No.: US 6,679,850 B1
(45) Date of Patent: Jan. 20, 2004

(54) BREAST STABILIZER

(76) Inventor: Henry T. Uhrig, 6717 Isla del Rey, El Paso, TX (US) 79912

( * ) Notice: Subject to any disclaimer, the term of this patent is extended or adjusted under 35 U.S.C. 154(b) by 0 days.

(21) Appl. No.: 10/231,518

(22) Filed: Aug. 30, 2002

(51) Int. Cl.[7] .............................. A61B 10/00; A61B 8/00
(52) U.S. Cl. ...................................... 600/562; 600/439
(58) Field of Search ................................ 600/562–568, 600/439; 606/57, 130; 269/1–3, 5–6, 46, 86, 203, 216–217, 292–293, 909

(56) References Cited

U.S. PATENT DOCUMENTS

| | | | |
|---|---|---|---|
| 3,971,950 A | | 7/1976 | Evans et al. .................. 250/451 |
| 4,691,333 A | | 9/1987 | Gabriele et al. ............... 378/37 |
| 5,820,552 A | | 10/1998 | Crosby et al. ............... 600/407 |
| 6,122,542 A | | 9/2000 | Lee et al. .................... 600/427 |
| 6,159,221 A | * | 12/2000 | Chaheres .................... 600/567 |
| 6,165,137 A | * | 12/2000 | Milliman et al. ............ 600/567 |
| 6,258,104 B1 | * | 7/2001 | Kreizman et al. ........... 606/130 |
| 6,270,506 B1 | * | 8/2001 | Sittek et al. ................. 606/130 |
| 6,304,770 B1 | * | 10/2001 | Lee et al. .................... 600/427 |
| 6,308,097 B1 | * | 10/2001 | Pearlman .................... 600/547 |
| 6,423,076 B1 | * | 7/2002 | Cardwell et al. ............ 606/130 |

FOREIGN PATENT DOCUMENTS

| | | | |
|---|---|---|---|
| WO | WO 02/36032 | 5/2002 | ........... A61B/19/00 |

* cited by examiner

Primary Examiner—Francis J. Jaworski
(74) Attorney, Agent, or Firm—Locke, Liddle & Sapp LLP; Kristen R. Paris

(57) ABSTRACT

A device for stabilizing the breast during a medical procedure having a base plate secured to support members, a column held by the support members and extending vertically upward beyond the base plate, a frictional engagement device releasably gripping the column and attached to a pressure plate, the pressure plate being positioned parallel to and above the base plate and movable along the column toward and away from the base plate using the frictional engagement device, the pressure plate having an aperture providing access to the breast, the aperture having internal beveled walls to guide a medical instrument. The breast is placed on the base plate and the frictional engagement device is used to move the pressure plate, allowing the pressure plate to contact the breast to securely hold the breast between the pressure plate and the base plate, making the medical procedure more accurate and efficient.

16 Claims, 7 Drawing Sheets

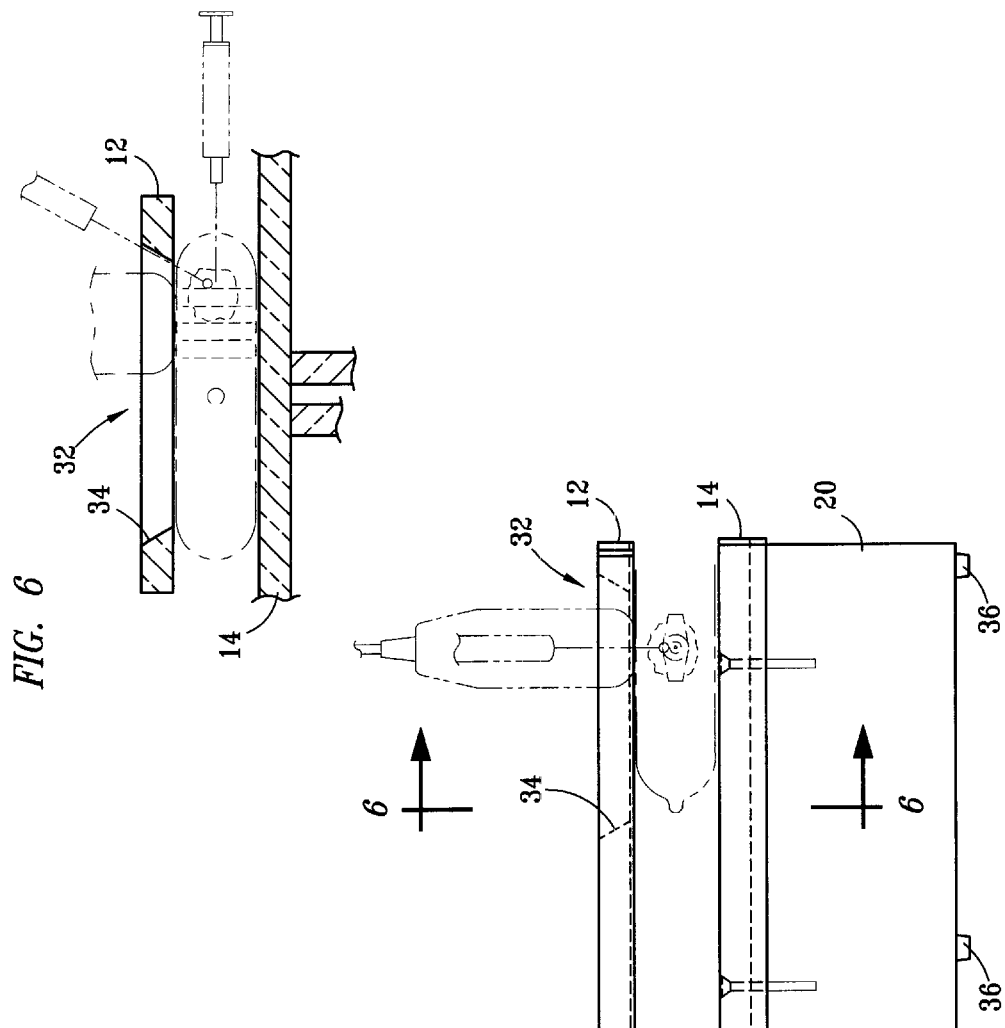

BREAST STABILIZER

BACKGROUND OF THE INVENTION

1. Field of the Invention

This invention relates to a device for stabilizing a breast during a medical procedure. More particularly, the device securely holds the breast for an ultrasound guided biopsy or cyst aspiration.

2. Description of Related Art

Biopsies or cyst aspirations on a breast are typically performed using a procedure commonly known as "freehand." The patient is recumbent and is usually turned obliquely to one side. The breast lies free and unsupported while ultrasound locates the lesion to be biopsied or aspirated. One way to perform "freehand" is to have an ultrasound technician hold the ultrasound transducer while the physician guides the needle into the breast and to the lesion. However, "freehand" can also be carried out by the physician alone, who manipulates the ultrasound transducer with one hand and the biopsy needle or other medical instrument with the other hand.

Performing "freehand," however, requires considerable experience and skill as well as time and effort. As most breasts are very mobile, because they contain fatty tissue giving them a soft consistency, it is often very difficult and time-consuming to manipulate the breast in order to introduce a biopsy needle or other medical instrument accurately and efficiently without a device securing the breast.

Components of a mammography machine can be used to stabilize the breast during a biopsy or cyst aspiration, making the biopsy or cyst aspiration more accurate and efficient. The breast is placed in a position as to do a cranio-caudal or top-to-bottom image of the breast and placed in the compression position. A compression plate with an aperture is then utilized to secure the breast while the biopsy or cyst aspiration is performed.

However, using a mammography machine for biopsies or cyst aspirations unnecessarily occupies the machine for a few hours. The machine instead could be producing life-saving mammograms. Further, many hospitals or clinics, because of their patient loads, cannot afford to have one of their mammography machines off-line and not producing mammograms for a few hours. Even if a mammography machine is purchased only for the purpose of performing biopsies or cyst aspirations, which can be expensive, or if the mammography machine is broken and only being used for biopsies or cyst aspirations, the extra machine takes up too much space. It is well known that most hospitals need every square inch of extra space.

Devices independent of mammography machines that secure the breast during medical procedures are known in the art. Such devices, however, have complicated parts, are hard to control, are bulky and intimidate the patient. A device used for stabilizing the breast during a biopsy or cyst aspiration is therefore needed that is independent of a mammography machine, that has simple yet reliable parts, is easy to use and control, is sturdy, is lightweight and portable. The device also needs to be comfortable, painless and not intimidating for the patient using the device. Lastly, the device needs to securely hold the breast in place during a biopsy or cyst aspiration, thereby making biopsies and cyst aspirations of the breast more accurate and efficient. These and other advantages are provided by the invention disclosed below.

SUMMARY OF THE INVENTION

A breast stabilizer is disclosed herein that is independent of a mammography machine and that renders a medical procedure, more specifically a biopsy or cyst aspiration of the breast, easier. The invention securely holds the breast between two plates thereby stabilizing the breast while a physician performs the biopsy or cyst aspiration. This allows the physician to perform the biopsy or cyst aspiration quickly and accurately without the breast moving.

The breast stabilizer of the invention comprises a base plate, pressure plate, support members, column and frictional engagement device. The base plate has an upper surface and a lower surface, the lower surface of the base plate being secured to the support members. Two of the four support members secure the column that extends vertically upward from the support members and beyond the base plate. The frictional engagement device releasably grips the column above the upper surface of the base plate. The frictional engagement device is connectable to the pressure plate, which slidably cooperates with the column and is positioned parallel to and above the upper surface of the base plate. Using the frictional engagement device, the pressure plate can be raised and lowered in a controlled manner relative to the base plate to secure the breast between the pressure plate and the upper surface of the base plate. The frictional engagement device uses micro-adjustments to move the pressure plate up and down the column and prevents movement of the pressure plate except when the physician or other operator desires to adjust the position of the plate relative to the base plate. For better access to the top of the breast, the pressure plate contains an aperture having internal beveled walls, used to guide a biopsy needle or other medical instrument. The base plate, pressure plate and support members are preferably made of a transparent polymeric material, and the base plate and pressure plate have rounded edges and corners to avoid injuries to the patient.

The patient may be seated upright or standing when the present invention is used. The breast is placed on the upper surface of the base plate below the raised pressure plate. The physician or other operator can then use the frictional engagement device to lower the pressure plate in a controlled manner. Once the pressure plate contacts the top of the breast, the pressure plate is lowered until the breast is securely held between the pressure plate and the upper surface of the base plate. The physician can then perform the biopsy or cyst aspiration without the breast shifting. When the physician has completed the biopsy or cyst aspiration, the pressure plate can then be raised using the frictional engagement device.

The present invention has simple but reliable parts, is lightweight, easily portable between rooms of a hospital or clinic and is sturdy due to the use of support members. The device is-easy to use and control, for example, because the frictional engagement device allows for the controlled movement of the pressure plate, which in turn allows the patient to be relaxed and unafraid of injury. The device is also comfortable, painless and not intimidating for the patient. The removal of tissue while using the present of invention is very successful, as the only lesions, perhaps unattainable are those located deep in the chest wall.

BRIEF DESCRIPTION OF THE DRAWINGS

The invention is further described and explained in relation to the following figures of the drawing wherein:

FIG. 5 is a side view of the breast stabilizer showing the pressure plate in a lowered position securely holding a breast (shown in phantom outline), and includes, in phantom outline, an ultrasound transducer and biopsy device positioned through the aperture and a needle introduced between the plates, the biopsy device and needle being in contact with a lesion;

FIG. 6 is a detail view taken along line 6—6 of FIG. 5, and shows, in phantom outline, the biopsy device and needle in a beam of the ultrasound transducer;

Like reference numerals are used to describe like parts in all figures of the drawings. The parts with primes are meant to illustrate a minor variation of a part with the same number.

DETAILED DESCRIPTION

Figure 1:
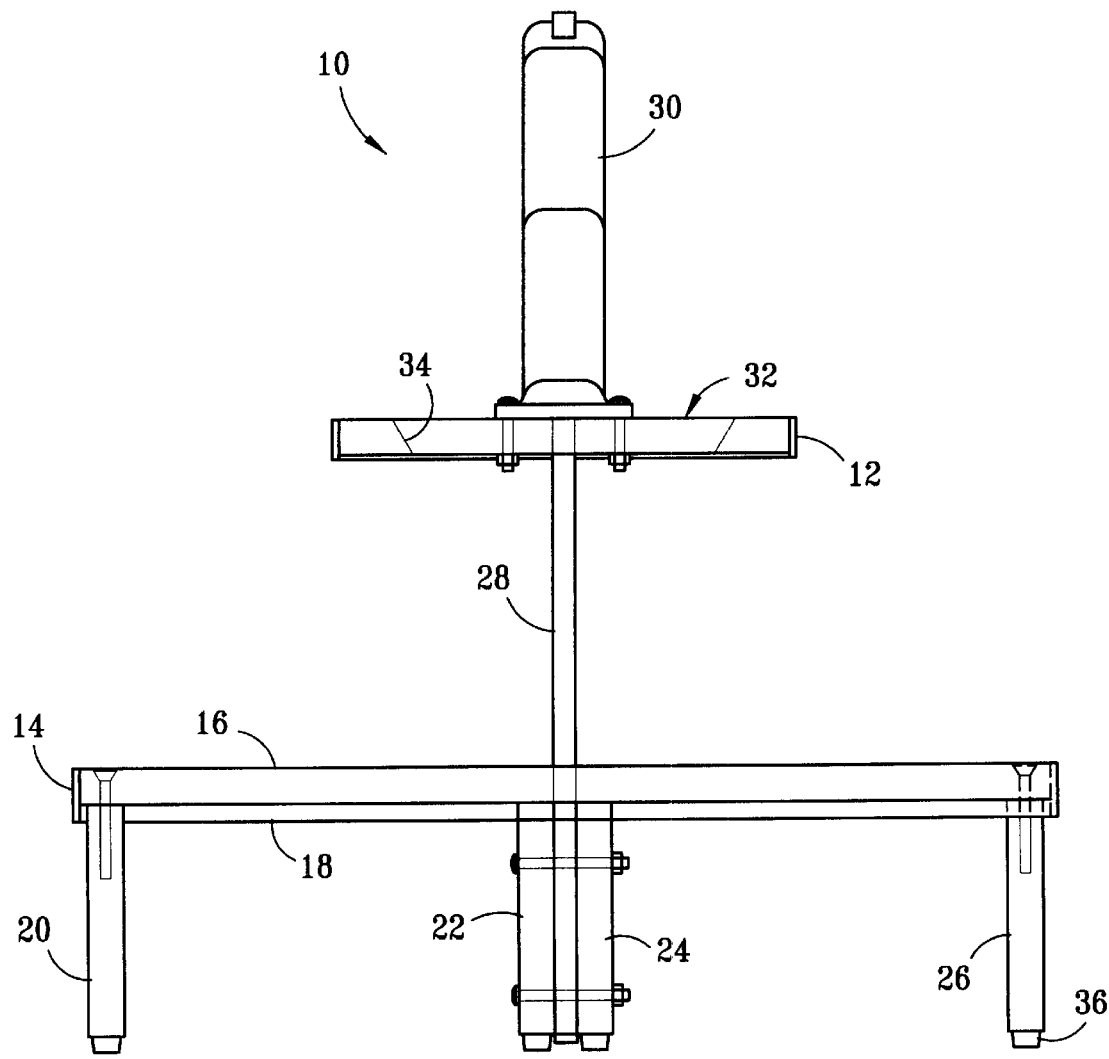
FIG. 1 is a front view of the breast stabilizer from the patient's side of the present invention.
Figure 2:
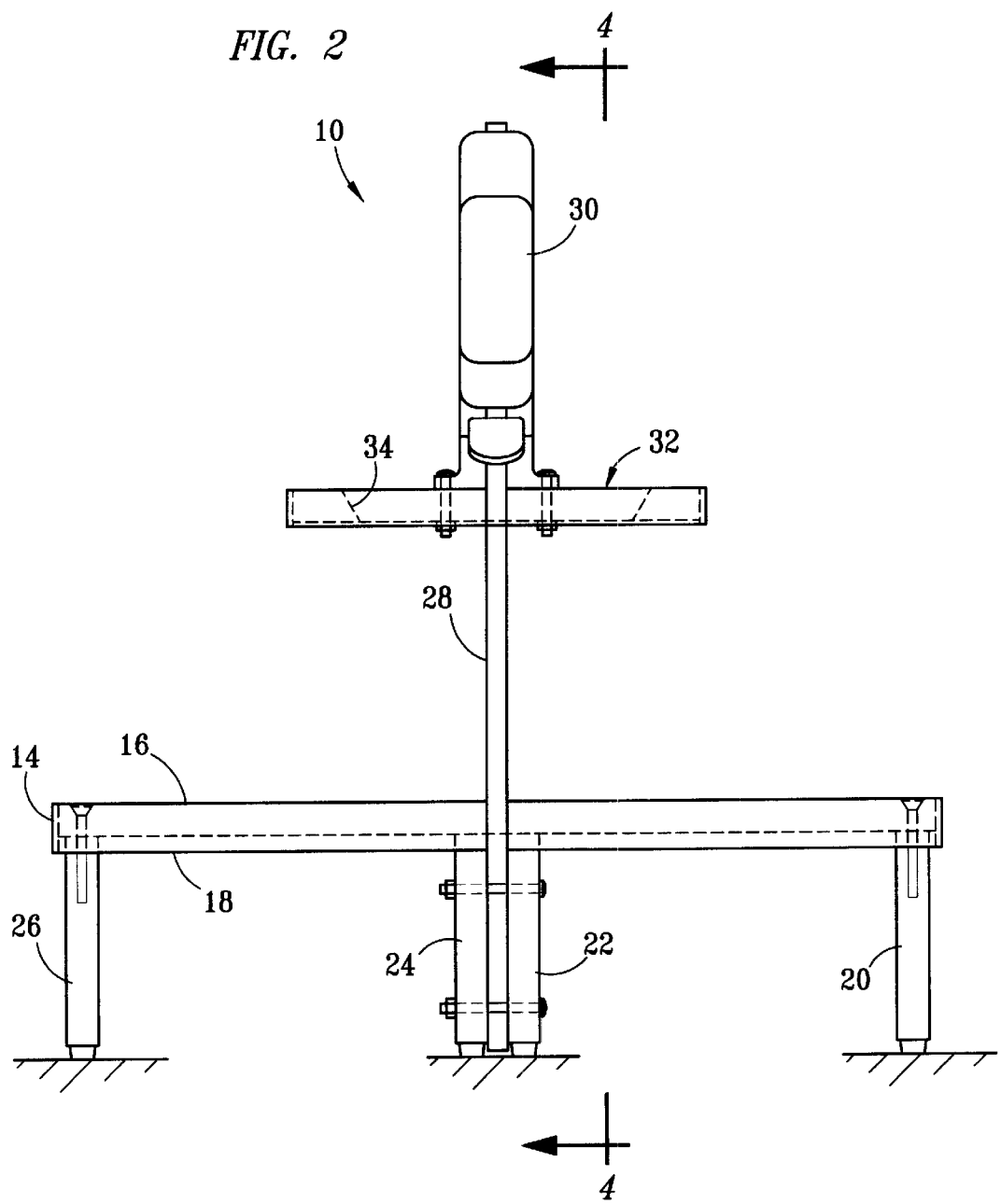
FIG. 2 is a front view of the breast stabilizer from the physician's or other operator's side and shows the breast stabilizer sitting on a flat surface.
Figure 3:
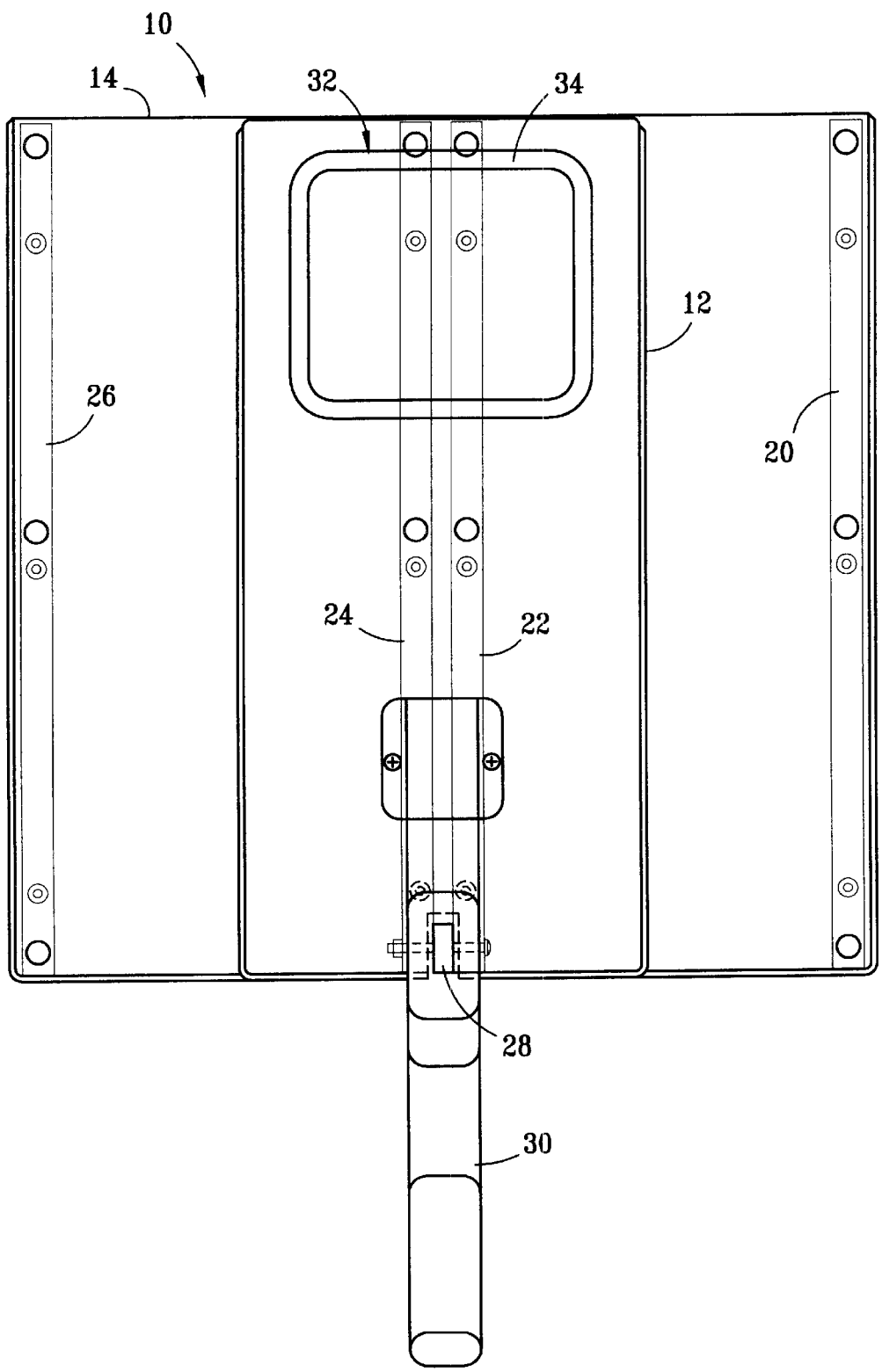
FIG. 3 is a top plan view of the breast stabilizer.

Referring to FIGS. 1–3 and 7, breast stabilizer 10 preferably comprises base plate 14, support members 20, 22, 24, 26, column 28, frictional engagement device 30 and pressure plate 12. Base plate 14 is generally rectangular, but can be any shape, such as a square. Base plate 14 preferably has flat upper surface 16 upon which a breast may be placed and lower surface 18. To support base plate 14, lower surface 18 of base plate 14 is secured to support members 20, 22, 24, 26 by screwing lower surface 18 to support members 20, 22, 24, 26. However, it should be understood that there are many ways of securing base plate 14 to support members 20, 22, 24, 26. Base plate 14 and support members 20, 22, 24, 26 may be molded together, fastened together or connected by any other similarly effective means.

Figure 8:
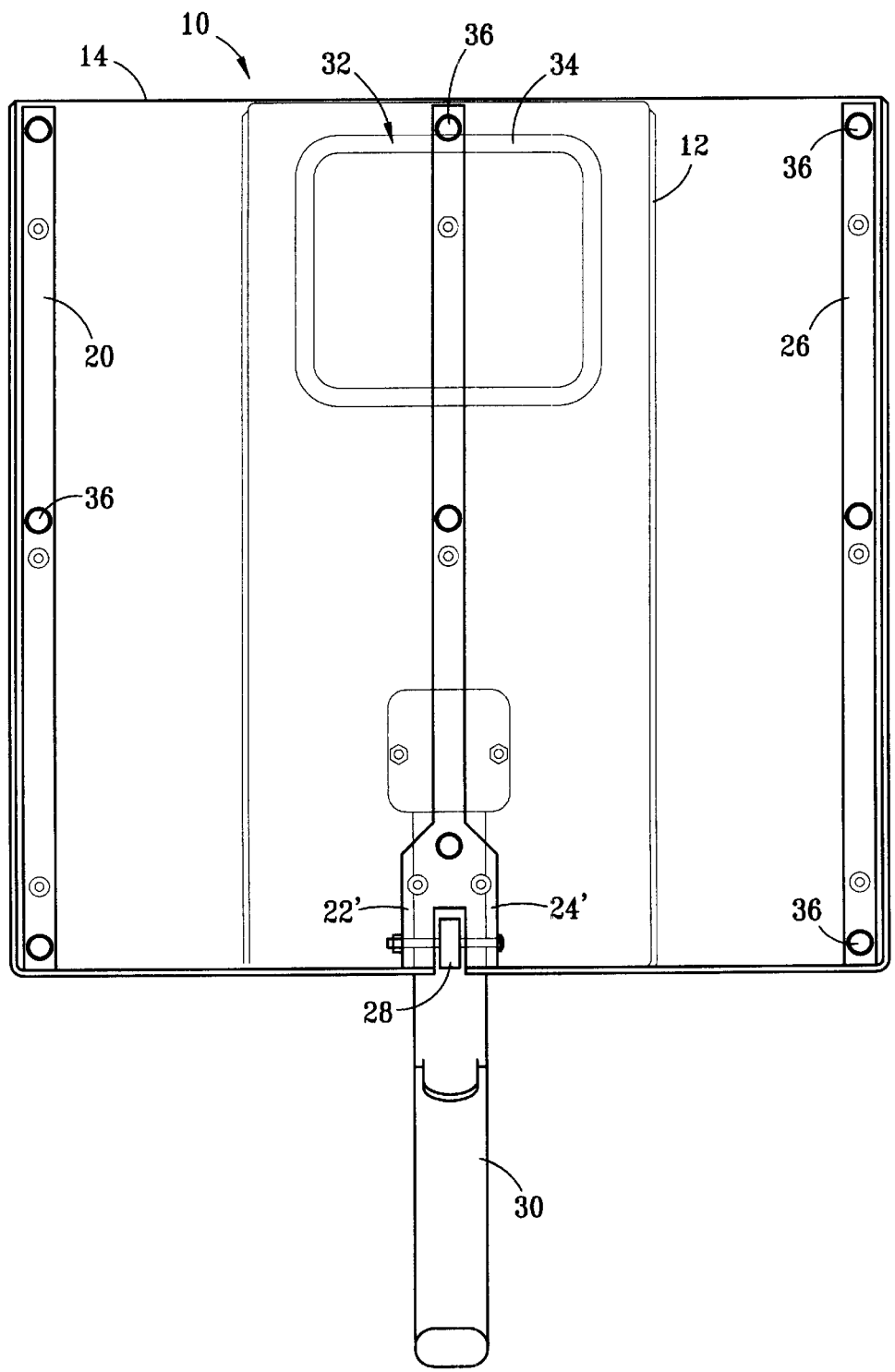
FIG. 8 is a bottom plan view of the breast stabilizer with modified support members.

Preferably, support members 20, 22, 24, 26 extend perpendicularly to lower surface 18 of base plate 14, are parallel to each other and each contains a solid, elongated portion that extends from one side of base plate 14 to the opposite side of base plate 14. However, support members 20, 22, 24, 26 can extend downward from lower surface 18 in any direction, including, but not limited to, an angular direction. Two of the four support members 22, 24 are positioned to contact column 28 and cooperate to secure column 28 therebetween, near the middle of one side of base plate 14, providing column 28 with enhanced structural support. Support members 22, 24 can be separate or can cooperate to form a clevis, as shown in FIG. 8 using reference numbers 22' and 24'. Preferably, support member 22, column 28 and support member 24 are screwed together. Support members 20, 22, 24, 26 can optionally be provided with underlying resilient adhesive-backed pads 36 to prevent breast stabilizer 10 from sliding when placed on a smooth surface.

Column 28 extends vertically upward from support members 22, 24 beyond base plate 14, and preferably through base plate 14. Column 28 is preferably made of metal, but it will be appreciated upon reading this disclosure that column 28 can be made of any material that supports the features of the present invention. Frictional engagement device 30 releasably grips column 28 above base plate 14, uses micro-adjustments to move up and down column 28 and is attached to pressure plate 12. A preferred frictional engagement device for use in the present invention is commercially available under the trademark "QUICK-GRIP" owned by American Tool Companies, Inc. However, frictional engagement device 30 can be any commercially available device that allows for controlled movement, and, thus need not be limited to any one specific type.

Pressure plate 12, which slidably cooperates with column 28 and is attached to frictional engagement device 30, is positioned parallel to and above base plate 14. Pressure plate 12 is generally rectangular, but can be any shape, such as a square. Using frictional engagement device 30, which preferably grips column 28 above pressure plate 12, pressure plate 12 can move in a controlled manner along column 28 towards and away from upper surface 16 of base plate 14. Frictional engagement device 30 desirably prevents pressure plate 12 from moving relative to base plate 14 except when the physician or other operator desires to adjust pressure plate 12 relative to base plate 14. Pressure plate 12 has aperture 32 with internal beveled walls 34 that help guide a biopsy needle or other medical instrument by providing wider approach angles and a resting surface for the biopsy needle or other medical instrument. Aperture 32 is desirably large enough that at least an ultrasound transducer and another medical instrument, including, but not limited to, a biopsy device or biopsy needle, can pass through aperture 32. Aperture 32 is preferably rectangular, but can be any shape including, but not limited to, a circle, a square or any other polygonal shape. When pressure plate 12 is in contact with the breast, aperture 32 allows the physician to have better access to the top of the breast. However, it should be appreciated that the physician can also access the sides of the breast not in contact with pressure plate 12 or base plate 14 without going through aperture 32.

Preferably, base plate 14, pressure plate 12 and support members 20, 22, 24, 26 are made of a moldable polymeric material. A transparent polymeric material that is resistant to alcohol stains that result from frequent cleaning is particularly preferred. The transparent material allows the physician or other operator to observe the compression of the breast under the pressure plate to determine the position of the breast and allows the physician to know when to stop adding additional pressure to the breast. The polymeric material, or any other material, used for base plate 14, pressure plate 12 and support members 20, 22, 24, 26 is thick enough to be sufficiently rigid. Column 28 extends far enough vertically to allow the maximum separation between pressure plate 12 and base plate 14 that is desired or needed. The corners and edges of base plate 14 and pressure plate 12 are preferably rounded so that the patient is comfortable and not injured when the breast is placed on base plate 14 or when pressure plate 12 is lowered to secure the breast.

Figure 4:
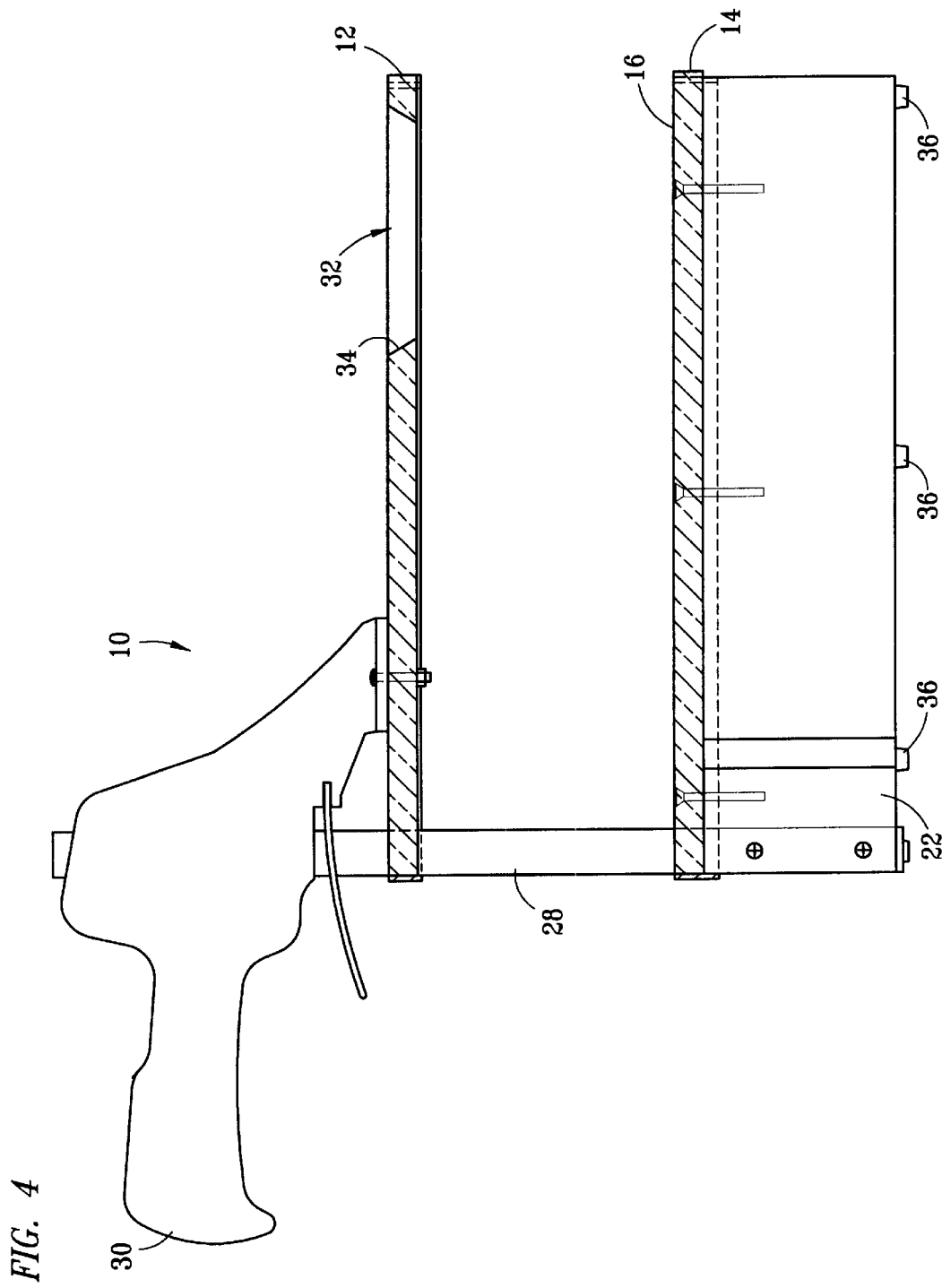
FIG. 4 is a cross-sectional view taken along line 4—4 of FIG. 2, and depicts the pressure plate in a raised position.
Figure 7:
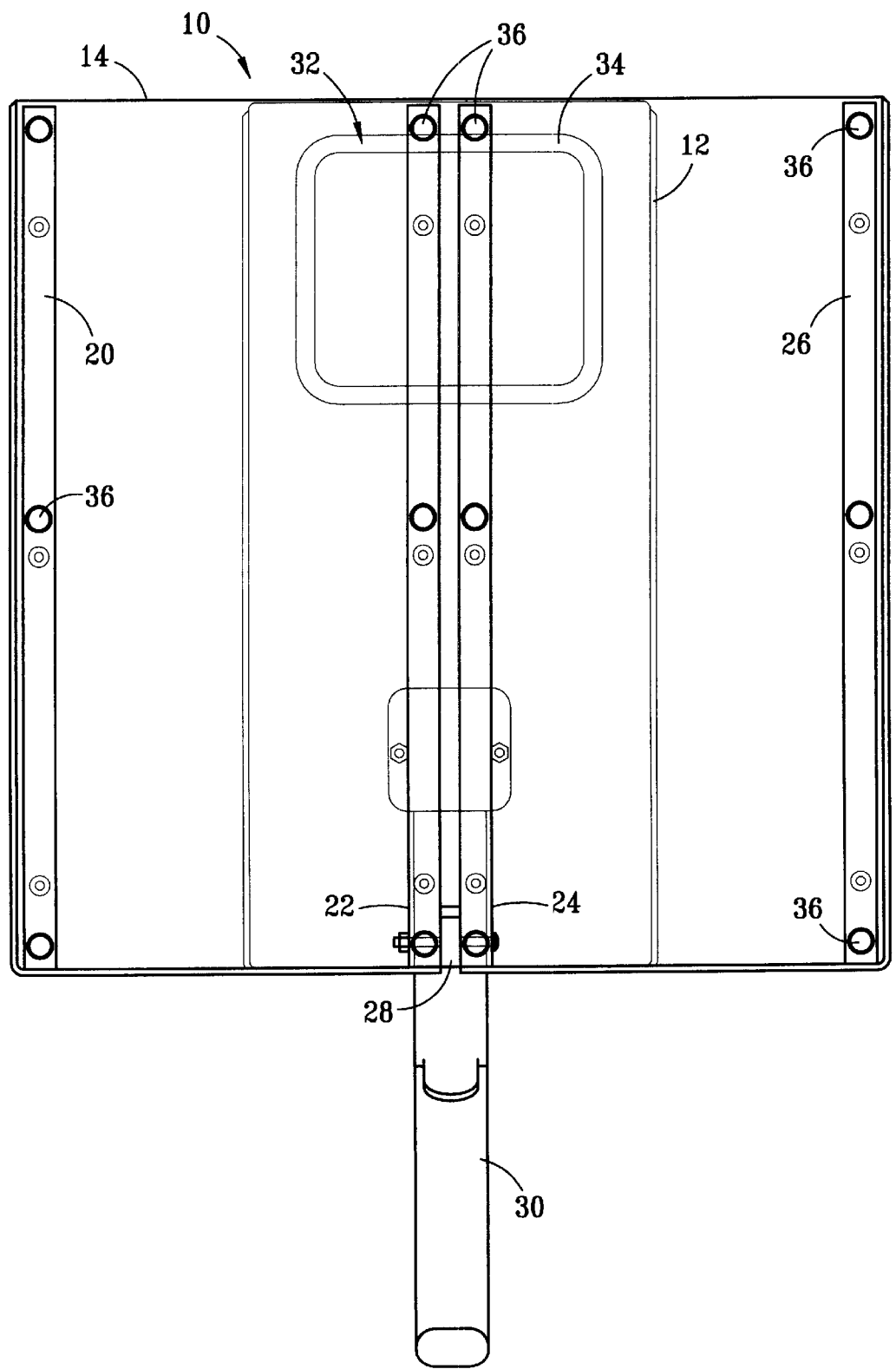
FIG. 7 is a bottom plan view of the breast stabilizer.

Breast stabilizer 10 of the invention can be used on a table with a flat surface or any other similar structure, and can be used while the patient is seated upright or standing. The breast is placed on base plate 14 when pressure plate 12 is in the raised position (see FIG. 4). The physician or other operator then uses frictional engagement device 30 to lower pressure plate 12 in a controlled manner. When pressure plate 12 contacts the breast, the physician or other operator lowers pressure plate 12 until the breast is securely held between pressure plate 12 and base plate 14 (see FIG. 5). The physician can now-perform a biopsy or cyst aspiration without the breast shifting. The physician has access to the top of the breast through aperture 32 or can access the sides of the breast that are not in contact with pressure plate 12 or base plate 14 without going through aperture 32 (as shown in FIGS. 5 and 6). When the physician has completed the biopsy or cyst aspiration, the physician or other operator can again use frictional engagement device 30 to raise pressure plate 12 away from the breast, releasing the breast.

Other alterations and modifications of the preferred embodiment described above will become apparent to those of ordinary skill in the art upon reading this disclosure, and it is intended that the scope of the invention disclosed herein be limited only by the broadest interpretation of the appended claims to which the inventor is legally entitled.

What is claimed is:

1. A device which is stand-alone with respect to components of a mammographic machine for stabilizing a breast during a medical procedure, the device comprising:

a base plate having an upper surface and a lower surface, the lower surface of the base plate secured to a plurality of support members, the support members extending downward from the lower surface of the base plate, at least two of the support members contacting a longitudinally extending column and cooperating to secure the column therebetween, the column extending vertically upward from the support members and beyond the base plate;

a frictional engagement device for releasably gripping the column above the upper surface of the base plate;

a pressure plate having an aperture with internal beveled walls for the guidance of a medical instrument, the pressure plate slidably cooperating with the column, connected to the frictional engagement device and positioned parallel to and above the upper surface of the base plate; wherein the pressure plate being movable towards and away from the upper surface of the base plate using the frictional engagement device, enabling the pressure plate to contact and securely hold the breast between the pressure plate and the upper surface of the base plate.

2. The device of claim 1 wherein the pressure plate, base plate and support members are made of a polymeric material.

3. The device of claim 2 wherein the polymeric material is resistant to alcohol stains.

4. The device of claim 2 wherein the polymeric material is transparent.

5. The device of claim 1 wherein the aperture is large enough to receive both an ultrasound transducer and another medical instrument.

6. The device of claim 1 wherein the aperture is generally rectangular.

7. The device of claim 1 wherein the support members have underlying resilient adhesive-backed pads.

8. The device of claim 1 wherein the base plate is secured to four support members.

9. The device of claim 1 wherein the at least two support members secure the column near the middle of one side of the base plate.

10. The device of claim 1 wherein the at least two support members cooperate to form a clevis.

11. The device of claim 1 wherein the frictional engagement device is releasably gripping the column above the pressure plate.

12. The device of claim 1 wherein the support members are parallel to each other.

13. The device of claim 1 wherein each support member has a solid, elongated portion that extends from one side of the base plate to an opposite side of the base plate.

14. The device of claim 1 wherein the support members extend perpendicularly to the lower surface of the base plate.

15. A method of using a device which is stand-alone with respect to components of a mammographic machine for stabilizing the breast during a medical procedure, the method comprising the steps of:

providing a base plate secured to support members;

providing a column that is secured between and in contact with two of the support members and that extends vertically beyond the base plate;

providing a pressure plate that slidably cooperates with the column above and parallel to the base plate and that has an aperture with internal beveled walls;

providing a frictional engagement device for releasably gripping the column when the pressure plate is properly adjusted relative to the base plate and that is attachable to the pressure plate;

placing a breast on the base plate; and manipulating the frictional engagement device to lower or raise the pressure plate along the column towards or away from the base plate enabling the pressure plate to contact and securely hold the breast between the pressure plate and the base plate.

16. The method of claim 15 comprising the additional step of applying an ultrasound transducer and another medical instrument within the aperture.

\* \* \* \* \*